United States Patent
Tapper et al.

(10) Patent No.: US 9,374,973 B2
(45) Date of Patent: *Jun. 28, 2016

(54) GRASS ENDOPHYTES

(75) Inventors: Brian Anthony Tapper, Palmerston North (NZ); Bruce Matheson Cooper, Kaikohe (NZ); Herrick Sydney Easton, Palmerston North (NZ); Lester Ronald Fletcher, Tai Tapu (NZ); David Edward Hume, Palmerston North (NZ); Geoffrey Alexander Lane, Palmerston North (NZ); Garrick Cecil Morland Latch, Palmerston North (NZ); Christopher Gerald Lee Pennell, Canterbury (NZ); Alison Jean Popay, Hamilton (NZ); Michael John Christensen, Palmerston North (NZ)

(73) Assignee: GRASSLANZ TECHNOLOGY LTD, Palmerston North (NZ)

(*) Notice: Subject to any disclaimer, the term of this patent is extended or adjusted under 35 U.S.C. 154(b) by 1253 days.

This patent is subject to a terminal disclaimer.

(21) Appl. No.: 13/179,056

(22) Filed: Jul. 8, 2011

(65) Prior Publication Data
US 2011/0262401 A1 Oct. 27, 2011

Related U.S. Application Data

(63) Continuation of application No. 11/293,889, filed on Dec. 2, 2005, now Pat. No. 7,976,857, which is a continuation of application No. PCT/NZ2004/000116, filed on Jun. 3, 2004.

(30) Foreign Application Priority Data

Jun. 3, 2003 (AU) .................. 2003902794

(51) Int. Cl.
*A01H 15/00* (2006.01)
*A01N 63/04* (2006.01)
*C12P 17/18* (2006.01)
*C12R 1/645* (2006.01)

(52) U.S. Cl.
CPC ............... *A01H 15/00* (2013.01); *A01N 63/04* (2013.01); *C12P 17/18* (2013.01); *C12R 1/645* (2013.01); *Y10S 435/911* (2013.01)

(58) Field of Classification Search
CPC ....... A01N 63/04; A01N 65/44; A01N 65/00; A01H 15/00; A01H 5/10; A01H 17/00; A01H 4/006; A01H 5/12; C12P 17/18; C12R 1/645; Y10S 435/911; C12N 15/52; C12N 15/8243; C12N 15/8286; C12N 1/14; C12N 1/00; C12N 15/1058; C12Q 1/6895
USPC .................. 424/405; 435/243, 410
See application file for complete search history.

(56) References Cited

U.S. PATENT DOCUMENTS

| | | | |
|---|---|---|---|
| 5,492,902 A | 2/1996 | Belofsky et al. | |
| 6,072,107 A | 6/2000 | Latch et al. | |
| 6,111,170 A | 8/2000 | Latch et al. | |
| 7,976,857 B2 * | 7/2011 | Tapper et al. | 424/405 |

FOREIGN PATENT DOCUMENTS

NZ 233083 7/2001

OTHER PUBLICATIONS

Australian Government Analytical Laboratories (AGAL) accession No. NM03/35819 (*Neotyphodium lolii* AR37), dated May 23, 2003.
Australian Government Analytical Laboratories (AGAL) accession No. NM03/35820 (*Neotyphodium lolii* AR40), dated May 23, 2003.
Ball, et al., "Effect of Selected Isolates of Acremonium Endophytes on Adult Black Beetle (*Heteronychus arator*) Feeding" *Proc 47th N.Z. Plant Protection Conf.* (1994): 227-231.
Ball, et al. 1997. Ergopeptine alkaloids and *Neotyphodium lolii*-mediated resistance in perennial ryegrass against *Heteronychus arator* (Coleoptera: Scarabaeidae). *Journal of Economic Entomology*, 90(5):1382-1391.
Barker, et al. 1993. Effect of water deficit on alkaloid concentrations in perennial ryegrass endophyte associations. In *Proceedings of the Second International Symposium on Acremonium/Grass Interactions*. Eds. Hume, D. E.; Latch, G. C. M.; Easton, H. S. AgResearch, New Zealand, pp. 67-71.
Belofsky, et al. 1995. Antiinsectan alkaloids: Shearinines A-C and a new paxilline derivative from the ascostromata of *Eupenicillium Shearii*. *Tetrahedron*, 51(14):3959-3968.
Blank, et al. 1992. Soilborne seedling diseases of tall fescue: Influence of the endophyte, *Acremonium coenophialum*. *Phytopathology*, 82(10):1089.
Bouton, et al. 2002. Reinfection of tall fescue cultivars with non-ergot alkaloid-producing endophytes. *Agronomy Journal*, 94(3):567-574.
Bultman, et al. 2003. Isolate-dependent impacts of fungal endophytes in a multitrophic interaction. *Oikos*, 102:491-496.
Crush, et al. 2004. Effect of different *Neotyphodium* endophytes on root distribution of a perennial ryegrass (*Lolium perenne* L.) cultivar. *New Zealand Journal of Agricultural Research*, 47:345-349.
de Jesus, et al. 1984. Structure elucidation of the janthitrems, novel tremorgenic mycotoxins from *Penicillium janthinellum*. *Journal of the Chemical Society, Perkin Transactions I.*, 4:697-701.
Elbersen, et al. 1996. Growth and water relations of field-grown tall fescue as influenced by drought and endophyte. *Grass and Forage Science*, 51:333-342.

(Continued)

*Primary Examiner* — Debbie K Ware
(74) *Attorney, Agent, or Firm* — Knobbe, Martens, Olson and Bear, LLP

(57) ABSTRACT

An endophyte or endophyte culture of *N. lolii* species is described that, in combination with a host grass does not cause typical symptoms of ryegrass toxicosis in grazing animals and also contains levels of compounds from the class of janthitrems epoxides to individually or in combination protect the host grass from pests or abiotic stresses or both. Uses and methods are also described to produce and characterize the combination as well as alternative uses for compounds from the class of janthitrem epoxide compounds.

16 Claims, No Drawings

(56) References Cited

OTHER PUBLICATIONS

Fletcher, L. R. 1999. "Non-toxic" endophytes in ryegrass and their effect on livestock health and production. In *Ryegrass Endophyte: An Essential New Zealand Symbiosis*. Grassland Research and Practice Series No. 7, pp. 133-139.

Fletcher, et al. 1999. The impact of endophyte on the health and productivity of sheep grazing ryegrass-based pastures. In *Ryegrass Endophyte: An Essential New Zealand Symbiosis*. Grassland Research and Practice Series No. 7, pp. 11-17.

Fletcher, et al. 2000. Using endophytes for pasture improvement in New Zealand. In Proceedings of The Grassland Conference 2000, 4th International Neotyphodium/Grass Interactions Symposium. Eds. Paul, V. H.; Dapprich, P. D., Universtät, Paderborn, pp. 149-162.

Gallagher, et al. 1980. The janthitrems: Fluorescent tremorgenic toxins produced by *Penicillium janthinellum* isolates from ryegrass pastures. *Applied and Environmental Microbiology*, 39(1):272-273.

Griffiths, et al. 1999. Non-radioactive AFLP fingerprinting for detection of genetic variation in *Epichloë/Neotyphodium* endophytes. Proceedings of the 11th Australian Plant Breeding Conference, Adelaide, vol. 2, pp. 212-213.

Latch, et al. 1985. Artificial infection of grasses with endophytes. *Annals of Applied Biology*, 107:17-24.

Leuchtmann, A. 1997. Ecological diversity in *Neotyphodium*-infected grasses as influenced by host and fungus characteristics. In *Neotyphodium/Grass Interactions*, Eds. Bacon, C. W.; Hill, N. S. Plenum Press, New York, pp. 93-108.

Moon, et al. 1999. Identification of Epichloë endophytes in planta by a microsatellite-based PCR fingerprinting assay with automated analysis. *Applied and Environmental Microbiology*, 65(3):1268-1279.

Penn, et al. 1993. Janthitrems B and C, two principal indole-diterpenoids produced by *Penicillium janthinellum*. *Phytochemistry*, 32(6):1431-1434.

Popay et al. "Cultivar and Endophyte Effects on a Root Aphid, *Aploneura Lentisci*, in Perennial Ryegrass." New Zealand Patent Protection. 60:223-227 (2007).

Popay, et al. 1995. Resistance to Argentine stem weevil in perennial ryegrass infected with endophytes producing different alkaloids. *Proc. 48th N.Z. Plant Protection Conf.*, pp. 229-236.

Prestidge, et al. 1985. Lolitrem B—A stem weevil toxin isolated from *Acremonium*-infected ryegrass. Proceedings 38th New Zealand Weed and Pest Control Conference, pp. 38-40.

Rowan, et al. 1986. Peramine, a novel insect feeding deterrent from ryegrass infected with the endophyte *Acremonium loliae*. *Journal of the Chemical Society. Chem. Commun.*, pp. 935-936.

Rowan, et al. 1990. Effect of fungal metabolite peramine and analogs on feeding and development of Argentine stem weevil (*Listronotus bonariensis*). *Journal of Chemical Ecology*, 16(5):1683-1695.

Rowan, et al. 1994. Utilization of endophyte-infected perennial ryegrasses for increased insect resistance. In *Biotechnology of Endophyte Fungi in Grasses*. Eds. Bacon, C. W., White, J. CRC Press, pp. 169-183.

Siegel, et al. 1990. Fungal endophyte-infected grasses: Alkaloid accumulation and aphid response. *Journal of Chemical Ecology*, 16(12):3301-3315.

Spiering, et al. 2002. Simplified extraction of ergovaline and peramine for analysis of tissue distribution in endophyte-infected grass tillers. *Journal of Agricultural and Food Chemistry*, 50:5856-5862.

Stuedemann, et al. 1988. Fescue endophyte: History and impact on animal agriculture. *Journal of Production Agriculture*, 1(1):39-44.

Tapper, et al. 1999. Selection against toxin production in endophyte-infected perennial ryegrass. In *Ryegrass Endophyte: An Essential New Zealand Symbiosis*. Grassland Research and Practice Series No. 7, pp. 107-111.

van Zijll de Jong, et al, "Development and characterization of EST-derived simple sequence repeat (SSR) markers of pasture grass endophytes" *Genome* (2003) 46: 277-290.

Wilkins, et al. 1992. Structure elucidation of janthitrem B, a tremorgenic metabolite of *Penicillium janthinellum*, and relative configuration of the A and B rings of janthitrems B, E, and F. *Journal of Agricultural and Food Chemistry*, 40(8):1307-1309.

di Menna, M.E.; Finch, S.C.; Popay, A.J.; Smith, B.L. 2012. A review of the *Neotyphodium lolii / Lolium perenne* symbiosis and its associated effects on animal and plant health, with particular emphasis on ryegrass staggers. *New Zealand Veterinary Journal* 60: 315-328.

Gallagher, R.T.; Hawkes, A.D.; Stewart, J.M. 1985. Rapid determination of the neurotoxin lolitrem B in perennial ryegrass by high-performance liquid chromatography with fluorescence detection. *Journal of Chromatography* 321: 217-226.

Miles, C.O.; Lane, G.A.; di Menna, M.E.; Garthwaite, I.; Piper, E.L.; Ball, O.J.-P.; Latch, G.C.M.; Allen, J.M.; Hunt, M.B.; Bush, L.P.; Min, F.K.; Fletcher, I.; Harris, P.S. 1996. High levels of ergonovine and lysergic acid amide in toxic *Achnatherum inebrians* accompany infection by an *Acremonium*-like endophytic fungus. *Journal of Agricultural and Food Chemistry* 44: 1285-1290.

Baldauf, M.W.; Mace, W.J.; Richmond, D.S. 2011. Endophyte-mediated resistance to black cutworm as a function of plant cultivar and endophyte strain in tall fescue. *Environmental entomology* 40: 639-647.

Tapper, B.A.; Lane, G.A. 2004. Janthitrems found in a *Neotyphodium* endophyte of perennial ryegrass. p. Poster/paper 301. In: Proceedings of the 5th International Symposium on *Neotyphodium/* Grass Interactions.

* cited by examiner

GRASS ENDOPHYTES

RELATED APPLICATIONS

This application is a continuation of and claims priority to co-pending U.S. application Ser. No. 11/293,889, filed on Dec. 2, 2005, entitled GRASS ENDOPHYTES, which is a continuation of and claims priority under 35 U.S.C. §120 to PCT Application No. PCT/NZ2004/000116, filed on Jun. 3, 2004, and published in English as WO 2004/106487 A2 on Dec. 9, 2004, which claims priority to Australian Patent Application No. 2003902794, filed on Jun. 3, 2003, the entire contents of each of which are incorporated herein by reference.

TECHNICAL FIELD

This invention relates to fungal endophytes and combinations of endophytes with grass plants. More particularly the invention relates to endophytes which form combinations with perennial, annual and hybrid ryegrasses and some other related grasses. Even more particularly the invention relates to combinations having reduced toxicity to grazing livestock as compared to cultivars of endophyte/ryegrass combinations in common use whilst still retaining resistance against pests and/or abiotic stresses.

BACKGROUND ART

Fungal endophytes of the genus *Neotyphodium* (formerly *Acremonium*) infect a number of temperate climate Pooideae grasses. The *Neotyphodium* endophytes can produce alkaloids which are considered to confer degrees of pest and possibly disease protection upon the plants in which they naturally occur (Rowan and Latch, 1994; Blank and Gwinn, 1992). Resistance to drought conditions has also been claimed (Elberson and West, 1996). The *Neotyphodium* endophytes are vertically transmitted through the seed of the grasses and no natural horizontal transmission has been established (Leuchtmann, 1997).

Many of the predominating natural endophyte infections of improved grass cultivars used for pastoral agriculture production also cause significant animal disorders, for example fescue toxicoses (Stuedemann and Hoveland, 1988) and ryegrass-endophyte toxicosis (Fletcher et al., 1999). These may be complex toxic reactions by animals to alkaloids produced under a range of plant growth conditions. Significant economic loss within pastoral agriculture systems can occur due to such animal toxicoses. On the other hand presence of at least some endophytes may be essential for the competitive persistence of the chosen grass in a pasture (Elberson and West, 1996, Fletcher and Easton, 2000).

It has also been found that grass lines can be artificially infected with selected endophytes. Axenic cultures of endophytes can be used to infect grass seedlings, grown initially under sterile conditions (Latch and Christensen, 1985), which can then be selected for desirable qualities, and multiplied for commercial use. Three significant examples of this technology have been developed by AgResearch Ltd: GREENSTONE™ tetraploid hybrid ryegrass with ENDOSAFE™ endophyte (Tapper and Latch, 1999, NZ Patent 233083); various perennial and hybrid ryegrasses with AR1 endophyte (Fletcher, 1999); and tall fescue cultivars with MaxQ™ (Bouton et al., 2002, U.S. Pat. No. 6,111,170).

Ryegrass-Endophyte Toxicosis

Perennial ryegrass infected with its common wild-type endophyte, grown for both forage and turf, frequently produces compounds of the lolitrem sub-group of indole diterpenes in concentrations in herbage sufficient to cause the serious animal disorder known as ryegrass staggers. Lolitrem B is considered the most abundant active substance and concentrations in excess of about 2 ppm of herbage dry matter may result in clinical symptoms of ryegrass staggers in grazing sheep, cattle, deer and horses.

The same ryegrass-endophyte associations also produce ergovaline and perhaps other ergot alkaloids which are believed to cause other symptoms in grazing sheep, cattle, deer and horses commonly associated with the ryegrass-endophyte toxicosis syndrome. These symptoms may include hyperthermia in warm humid conditions as evidenced by increased rectal temperatures and respiration rates and depressed basal prolactin levels.

These responses are likely to be elicited at ergovaline concentrations in ryegrass pastures above 0.5 ppm. Ergovaline is also believed to be responsible for the depressed growth rates associated with the toxicosis syndrome. Increased faecal moisture and faecal soiling in sheep is also associated with ryegrass-endophyte toxicosis but causes have not been ascribed to any particular toxins.

The ryegrass staggers symptoms and overall effect of lolitrems may be enhanced by the presence in herbage of other toxins such as ergovaline.

Both lolitrem B and ergovaline concentrations tend to be higher in leaf sheath and seed heads of perennial ryegrass than in the roots or leaf blade. They also undergo seasonal variation with peaks in summer to autumn.

Enhanced Plant Protection with Reduced Toxicosis

Endophytes confer degrees of protection to host plants against biotic and abiotic stress. Some endophyte-derived alkaloids are known to be toxic or deterrent to insect pests. Peramine is a feeding deterrent for and lolitrem is toxic to Argentine stem weevil, (Listronotus bonariensis) (Rowan et al., 1990; Prestidge and Gallagher 1985). Ergovaline is deterrent to black beetle (Heteronychus arator) (Ball et al., 1997). Where these alkaloids are absent or in very low concentration in plants, infestation by such pests become a problem. Hence it can be seen from the above discussion that it is desirable to have a ryegrass that has low mammalian toxicity but which also contains deterrent and/or insecticidal compounds to help avoid insect or other pest problems.

It is an object of the present invention to provide an endophyte which produces alkaloid compounds in herbage of a host plant in a manner such that the usual combinations and concentrations of alkaloids in herbage as generally consumed by grazing animals in common farming practice does not cause practical toxicosis symptoms. It is a further object of the present invention to provide an endophyte which produces alkaloid compounds in herbage of a host plant that protects the grass from pasture and/or turf pests relative to equivalent endophyte-free grass.

It is a further object of the invention to provide an endophyte which does not produce detectable levels of toxins from the lolitrem group or ergovaline group.

It is a further object of the invention to provide an endophyte from the genus *Neotyphodium* that, in combination with a host grass, gives superior pest protection for forage and/or turf uses compared to either equivalent endophyte-free grass or grass infected with common wild-type *Neotyphodium lolii*.

It is a further object of the invention to provide an endophyte which produces compounds from the class of janthitrem epoxides.

It is a still further object of the present invention to address the foregoing problems or at least to provide the public with a useful choice.

All references, including any patents or patent applications, cited in this specification are hereby incorporated by reference. No admission is made that any reference constitutes prior art. The discussion of the reference states what their authors assert, and the applicants reserve the right to challenge the accuracy and pertiency of the cited documents. It will be clearly understood that, although a number of prior art publications are referred to herein, this reference does not constitute an admission that any of these documents forms parts of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

According to one aspect of the present invention there is provided an isolated endophyte of $N.$ $lolii$ species, selected from the group consisting of: AR37; AR40; variations in $N.$ $lolii$ species as exemplified by AR37; variations in $N.$ $lolii$ species as exemplified by AR40; and combinations thereof; AR37 and AR40 cultures deposited on 23 May 2003 at the Australian Government Analytical Laboratories (AGAL) accession number NM03/35819 (AR37) and NM03/35820 (AR40);
- characterised in that, when the $N.$ $lolii$ species is in combination with a host grass, said endophyte will not produce sufficient levels of a compound or compounds to adversely affect the health and performance in grazing animals;
- and further characterised in that said endophyte produces sufficient levels of a compound or compounds to individually or in combination protect the host grass from pests or abiotic stresses or both;
- and further characterised in that the host grass is artificially inoculated with the endophyte.

According to a further aspect of the present invention there is provided an isolated endophyte culture of $N.$ $lolii$ species, selected from the group consisting of: AR37; AR40; variations in $N.$ $lolii$ species as exemplified by AR37; variations in $N.$ $lolii$ species as exemplified by AR40; and combinations thereof;
- characterised in that, when the $N.$ $lolii$ species is in combination with a host grass, said endophyte will not produce sufficient levels of a compound or compounds to adversely affect the health and performance in grazing animals;
- and further characterised in that said endophyte produces sufficient levels of a compound or compounds to individually or in combination protect the host grass from pests or abiotic stresses or both;
- and further characterised in that the host grass is artificially inoculated with the endophyte culture.

Preferably, in the endophyte or endophyte culture described above, the compound or compounds produced by the endophyte that confers protection to the host grass is an indole compound from the class of janthitrem epoxides.

In the present invention, the endophytes described above do not produce the hitherto known toxic alkaloids lolitrem B and ergovaline at levels in excess of 2 ppm lolitrem B and 0.5 ppm ergovaline. Preferably the lolitrem B and ergovaline levels are below detection levels of less than 0.1 ppm of dry matter.

The endophytes described above do however, produce sufficient levels of other substances to protect the host grass from pests or abiotic stresses (such as water deficit) or both. In particular, the endophyte-infected ryegrass produces a group of indole diterpene derivatives from the class of janthitrem epoxide compounds not formerly observed and identified in endophyte-infected grasses. It is the understanding of the applicant that these compounds confer protection from pest predation upon the host grass plants and the grass-dominant pasture or turf as a whole without causing toxicosis of practical significance.

Preferably, the host grass is a perennial, annual or hybrid ryegrass. Most preferably, these are selected from the species: $Lolium$ $perenne$; $Lolium$ $multiflorum$; $Lolium \times hybridum$.

Preferably, the toxicosis which is avoided is ryegrass-endophyte toxicosis. Most preferably the toxicosis is caused by an ergovaline toxin or a lolitrem toxin or a combination of ergovaline and lolitrem toxins.

Preferably, the abiotic stress is a water deficit.

Preferably the endophyte culture, if used, is an axenic culture.

Preferably, the endophyte culture, if used, has the same characteristics with respect to taxonomic classification, plant infectivity, alkaloid production, animal performance, and plant protection properties as the endophyte itself.

According to another aspect of the present invention there is provided a combination of the endophyte as described above, and a host grass.

According to another aspect of the present invention there is provided a combination of the endophyte culture as described above, and a host grass.

According to another aspect of the present invention there is a combination, substantially as described above, achieved by the breeding, crossing, hybridisation, selection, or genetic modification of grass containing the endophyte or endophyte culture.

According to another aspect of the present invention there is provided a combination of the endophyte or endophyte culture as described above, and a host grass, wherein the grass has enhanced root growth and more tillers in comparison to a host grass without endophyte infection.

According to another aspect of the present invention there is provided a combination of the endophyte or endophyte culture as described above, and a Pooideae grass.

According to another aspect of the present invention there is provided a combination of the endophyte or endophyte culture as described above, and a Pooideae grass wherein the combination produces compounds from the class of janthitrem epoxides in the grass and not more than 0.1 ppm of ergovaline in the dry matter of whole herbage.

According to another aspect of the present invention there is provided a combination of an endophyte as described above and a Pooideae grass wherein the combination has features selected from the group consisting of: enhancement of pest protection; resistance to insects; pasture persistence; and combinations thereof.

According to another aspect of the present invention there is provided a combination of an endophyte as described above and a Pooideae grass wherein the combination has the features of enhancement of grazing animal growth, and increased animal productivity in comparison with grass infected with known endophytes capable of inducing the disorder known as ryegrass-endophyte toxicosis.

According to another aspect of the present invention there is provided a combination of an endophyte or endophyte culture as described above and a host grass wherein the pest to which increased resistance is conferred on the host grass is selected from the group consisting of: root aphid (Aploneura lentisci); mealy bug (Balanococcus poae); Argentine stem weevil (Listronotus bonariensis); black beetle (Heteronychus arator); porina (Wiseana cervinata); and combinations thereof.

According to yet another aspect of the present invention there is provided seeds of a host grass infected with the endophyte as described above.

According to yet another aspect of the present invention there is provided an indole compound from the class of janthitrem epoxides produced from a host grass infected with the endophyte culture as described above.

According to yet another aspect of the present invention there is provided the use of a compound from the class of janthitrem epoxides as described above as a pesticide.

According to yet another aspect of the present invention there is provided the use of a compound from the class of janthitrem epoxides as described above as an insecticide.

According to a yet another aspect of the present invention there is a method of identifying endophytes of the group exemplified by AR37 and AR40 which includes the steps of:
(a) growing seed, preferably from collections of grass seed;
(b) harvesting and drying samples of herbage;
(c) obtaining a solvent extract from the dried herbage;
(d) examining such solvent extracts for the purposes of determining the presence of compounds of the janthitrem class of indole diterpenes (as described below) and the absence of compounds of the lolitrem class of indole diterpenes and the absence of ergovaline at detection levels of 0.1 ppm of dry matter by procedures selected from the techniques of high pressure liquid chromatography; reverse-phase chromatography; flash chromatography; UV light absorption; fluorescence; nuclear magnetic resonance; and mass spectrometry.

According to a yet another aspect of the present invention there is a method of characterising endophytes of the group exemplified by AR37 by application of microsatellite polymerase chain reaction amplification and product size analysis applied to DNA extracts of either endophyte in planta; endophyte; endophyte in a culture; and combinations thereof.

The invention is the combination of examples of a class of N. lolii endophyte and improved plant cultivars by artificial inoculation to produce grass which do not cause symptoms of toxicosis by way of the ergovaline toxin but which contain indole diterpene compounds which continue to protect the host grass from pests or abiotic stresses (such as water deficit) or both.

The invention also incorporates the methods of characterising endophytes of the class of this invention by examination of the properties of the endophytes in culture and in association with grass hosts.

The invention has been achieved by understanding the biology of endophytes of temperate climate grasses, isolating selected endophytes of interest, inoculating the endophytes into surface-sterilised seedlings of grasses, re-evaluating alkaloid production, multiplying seed, evaluating for agronomic factors, testing for animal production, evaluating for any evidence of animal disorders such as ryegrass toxicosis, hyperthermia, or prolactin hormone depression.

The invention consists of the foregoing and also envisages constructions of which the following are examples.

BEST MODES FOR CARRYING OUT THE INVENTION

Culture Conditions and Description

The endophytes of this invention are strains from collections of seed of perennial ryegrass originally sourced from France. Seed from many various ryegrass collections from many countries were examined for the presence of endophyte by seed squash technique. A few plants for each seed sample, where endophyte was shown to be present, were grown for a few weeks in glasshouse conditions and re-tested for endophyte presence in their leaf sheaths.

The endophytes from plants with chemotypes of interest, primarily those not producing lolitrem B or ergovaline were isolated and grown in culture according the method of Latch and Christensen (1985). The endophytes of this invention are held in seed stocks, a culture collection, or in cloned plants at the AgResearch Ltd site in Palmerston North, New Zealand. The cultures are also deposited at the Australian Government Analytical laboratories in Sydney, Australia.

All strains of endophyte of this invention can be accommodated within a single sub-grouping of the species *Neotyphodium lolii*. The isolates when grown on potato dextrose agar at 22° C. are typically slow growing (radial growth approximately 0.1-0.3 mm per day) with colonies typically white and cottony, becoming fawn with age. Conidia have not been observed.

Inoculations

Axenic cultures of endophyte AR37 as an example of this invention were successfully inoculated (Latch and Christensen, 1985) into seedlings grown from surfaced sterilised seed of perennial ryegrass cultivars *Lolium perenne*, for example Grasslands Nui and various experimental lines, generally with a satisfactory success rate usually in excess of 5% of attempts. Similarly annual ryegrasses *Lolium multiflorum*, for example Grasslands Moata, and Corvette, and hybrid ryegrasses *Lolium×hybridum* have been successfully inoculated for further examination with the chemotype characteristics of the combinations substantially the same as for perennial ryegrasses.

Chemotype Identification

Basal parts of endophyte-infected tillers were freeze dried, sometimes milled, and extracted and analysed qualitatively for the presence or absence of peramine, lolitrems and ergovaline by high performance liquid chromatography (HPLC) using minor modifications of the methods of Barker et al., (1993) and Spiering et al., 2002. Some endophytes from such selections lacking both lolitrems and ergovaline were isolated, classified by culture attributes, and generally re-inoculated into seedlings of endophyte-free perennial ryegrass, cultivar Grasslands Nui, as a typical improved pasture host for comparative purposes. Samples from such plants at various stages of growth were analysed in more detail for alkaloid production. Following seed multiplication two groups of endophyte-grass combinations (with and without peramine in excess of 5 ppm) were tested in field plot trials to further determine their general agronomic qualities, persistence, and practical resistance to insect predation. Some endophytes, not of this invention, produce peramine but not lolitrems nor ergovaline and are the subject of U.S. Pat. No. 6,072,107.

The endophytes of this invention are of a class that does not produce lolitrem B (or other closely related lolitrems of similar chromatographic and fluorescence properties) or ergovaline at detection levels of 0.1 ppm of herbage dry matter. Neither do they normally produce peramine at a detection level of 1 ppm of herbage dry matter.

Identification of New Alkaloids

The endophytes of this invention produce indole diterpenes not seen before from any grass infected with endophytes. Typically 50 mg portions of ground freeze dried herbage of plants infected with these endophytes were extracted for 1 hour with 1 ml of dichloroethane-methanol 9:1 by volume, and the extract collected by centrifugation or filtration. The extracts were examined for the presence or absence of lolitrems by normal phase HPLC, for example with Alltima silica 150×4.6 mm columns (Alltech Associates, Deerfield, Ill.) and dichloromethane-acetonitrile, 7:1 by volume at 1 ml/min using fluorescence detection (excitation 265 nm, emission 440 nm). Two fluorescent peaks were observed with the endophytes of this invention that are not characteristic of the N. lolii endophytes normally producing lolitrems. One of the peaks (A) was less retained than lolitrem B while another peak (B) was more retained. The same general pattern peaks was observed for extracts of herbage containing endophytes AR37 and AR40.

Extracts were also analysed by reverse phase HPLC, typically with a Prodigy 150×4.6 mm column (Phenomenex, Torrance, Calif., USA) and with a solvent mixture of typically 5.6:1 (v/v) acetonitrile:aqueous ammonium acetate buffer (0.005 M) adjusted to pH 6 with acetic acid. The solvent flow rate was 1 ml/min, and eluted peaks were detected by fluorescence (excitation 265 nm, emission 440 nm or excitation 333 nm, emission 385). The order of elution was reversed and resolution enhanced in comparison to the above normal phase separation. The fluorescent peaks identified here as components I, II, III, and IV had retention times 7.7, 21.5, 24.2, and 25.1 min respectively for the above typical separation conditions. The normal phase peak B corresponded to reverse phase component I while the normal phase peak A resolved into three components II, III, and IV. The chemical identity of these components was further investigated.

UV and fluorescence spectra of components I, II, III, and IV were obtained by reverse phase HPLC using diode array and fluorescence stopped-flow techniques (Shimadzu SPD-M10A and RF-10A detectors) with spectral maxima as in Table 1. These data compare substantially to the spectra reported for the indole diterpene class of janthitrems (Gallagher, 1980; de Jesus et al., 1984) or related shearinines (Belofsky, 1995).

TABLE 1

UV absorption and fluorescence spectral peaks

| Component | UV $\lambda_{Max}$ nm | Fluorescence $\lambda_{Em\ Max}$ nm ($\lambda_{Ex}$ 260 nm) |
|---|---|---|
| I | 259, 333 | 381 |
| II | 259, 333 | 383 |
| III | 259, 333 | 387 |
| IV | 259, 333 | 384 |

HPLC with mass spectrometry (LC-MS) was performed using reverse phase chromatography with electrospray ionisation (ESI) (Shimadzu QP-8000α detector) and with variations of scan range and deflector voltage to induce and explore ion fragmentation. Table 2 lists the m/z of the indicated MH$^+$ ions together with major fragment ions. The loss of a fragment of mass 58 (assigned here as a loss of Me$_2$CO) has been reported for EI MS of janthitrem C (Penn et al., 1993) and shearinine B (Belofsky, 1995).

TABLE 2

Mass spectral peaks from ESI LC-MS

| | ESI mass spectral peak attributions | | | | |
|---|---|---|---|---|---|
| Component | MH$^+$ m/z | MH$^+$ —H$_2$O | MH$^+$ —Me | MH$^+$ —Me$_2$CO | MH$^+$ —C$_5$H$_9$ |
| I | 646.5 | 628.4 | — | 588.3 | — |
| II | 670.5 | — | 655.1 | 612.4 | 600.95 |
| III | 672.5 | — | — | 614.6 | — |
| IV | 714.5 | — | — | 656.3 | — |

The further isolation and characterisation of component I was achieved by extracting 715 g of perennial ryegrass seed infected with endophyte AR37 with 3 liters of dichloromethane (DCM) at ambient temperature with stirring for 1.5-2 hr followed by a further 2 liters of DCM similarly treated. The combined extract was concentrated under reduced pressure and redissolved in hexane for a cycle of flash chromatography (Merck Silica Gel 60 0.040-0.063 mm, 170 g, 85 mm i.d.) with elution in 500 ml volume steps of hexane: DCM, DCM, DCM:acetonitrile (in proportions 19:1, 9:1, 4:1, and 1:1) and acetonitrile (MeCN). The fraction eluting with DCM:MeCN (4:1) was enriched with I and was evaporated to dryness (0.04 g), redissolved in a small volume of DCM: MeCN (4:1) and coated on to C-18 silica gel (2 g). This was put on top of a reverse phase silica gel flash column (Alltech octadecyl coated, 32 g, 28 mm i.d.) and fractions were eluted with 70 ml volumes of MeCN:H$_2$O in steps (1;1, 7:3, 4:1, 4:1, 9:1), MeCN, and DCM. The second MeCN:H$_2$O 4:1 fraction enriched in I was concentrated and used in two portions for flash chromatography on amino-coated silica (Analytichem Sepralyte Primary Secondary Amine, 2.1 g, 11 mm i.d.). Fractions were eluted with 5 ml volumes of MeCN:H$_2$O (1:1) and MeCN:H$_2$O (7:3). The MeCN:H$_2$O (1:1) fractions were concentrated to reduce volume, absorbed on a C-18 SPE column (2 g, 11 mm i.d.), eluted with MeCN and concentrated for examination by high resolution mass spectrometry and $^1$H and $^{13}$C NMR.

The high resolution mass spectrum obtained on a VG 70-250S mass spectrometer with a DCI probe yielded characterising ions with m/z 645.3647 (M$^+$) (calculated for C$_{39}$H$_{51}$NO$_7$: 645.3665) and m/z 630.3451 (M$^+$–Me) (calculated for C$_{38}$H$_{48}$NO$_7$: 630.3431).

Samples of I were examined in nuclear magnetic resonance (NMR) experiments to support a proposed structure of I which is also consistent with the high resolution masses.

NMR spectra were recorded in deuterioacetone ((CD$_3$)$_2$CO) solvent on a Bruker AC400 spectrometer. Chemical shifts are reported relative to TMS. The experiments included one-dimensional $^{13}$C (100.62 MHz) and $^1$H (400.13 MHz) spectra together with short-range and long range proton-proton (COSY) and proton-carbon correlation coupling (HMBC and HMQC) spectra. Signals were assigned by comparison with published NMR data for janthitrems (de Jesus et al., 1984; Wilkins et al., 1992; Penn et al., 1993) and shearinines (Belofksy et al., 1995), supported by the correlation data.

The proposed structure may be considered an epoxide of the known janthitrem G (de Jesus et al., 1984) and hence trivially named as 11,12-epoxy-janthitrem G (Figure 1).

The structure and numbering system for I is:

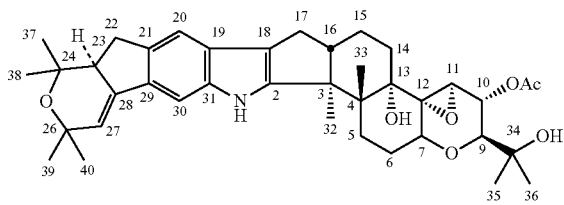

The supporting chemical shift data is in Table 3.

TABLE 3

| Atom | $^{13}C$ | $^1H$ |
|---|---|---|
| 2 | 154.3 | |
| 3 | 51.1 | |
| 4 | 42.6 | |
| 5 | 26.4 | 1.62, 2.60 |
| 6 | 28.2 | 1.80, 2.21 |
| 7 | 71.8 | 4.17 |
| 9 | 76.0 | 3.45 |
| 10 | 68.2 | 5.14 |
| 11 | 61.8 | 3.52 |
| 12 | 70.8 | |
| 13 | 77.4 | |
| 14 | 29.7 | 1.58 |
| 15 | 21.0 | 1.50, 1.90 |
| 16 | 50.3 | 2.70 |
| 17 | 27.2 | 2.31, 2.60 |
| 18 | 116.3 | |
| 19 | 127.2 | |
| 20 | 113.8 | 7.13 |
| 21 | 136.4 | |
| 22 | 32.0 | 2.63, 3.06 |
| 23 | 49.3 | 2.82 |
| 24 | 74.2 | |
| 26 | 72.4 | |
| 27 | 119.1 | 5.90 |
| 28 | 140.8 | |
| 29 | 133.0 | |
| 30 | 103.5 | 7.36 |
| 31 | 140.4 | |
| 32 | 16.0 | 1.35 |
| 33 | 18.3 | 1.16 |
| 34 | 69.9 | |
| 35 | 26.1 | 1.13 |
| 36 | 26.3 | 1.12 |
| 37 | 22.0 | 1.05 |
| 38 | 30.1 | 1.25 |
| 39 | 31.8 | 1.32 |
| 40 | 29.9 | 1.27 |
| Acetate Me | 20.8 | 2.09 |
| Acetate CO | 170.0 | |

By comparison and analysis of the UV, fluorescence and mass spectra we propose structures for II-IV:

II: The 10-deacetyl-10,34-(3-methylbut-2-enyl acetal) derivative of I.

III: The 10-deacetyl-34-O-(3-methylbut-2-enyl) derivative of I.

IV: The 34-O-(3-methylbut-2-enyl) derivative of I.

Genotype Characterisation of Endophyte

All endophytes of this invention so far tested are characterised by DNA "fingerprinting" (selected polymorphic microsatellite loci and/or AFLP technique) as belonging to a sub-group of *Neotyphodium lolii*.

Samples of about 50 mg fresh or 15 mg dry basal tiller were used for the extraction of DNA using FastDNA kit for plants (Bio 101, Vista, Calif.) using procedures recommended with the kit. Alternatively genomic DNA was extracted from cultured endophyte (Moon et al., 1999). Microsatellite PCR amplification was performed using primer pairs labelled with fluorescent dyes, B10.1 (5'-TET)/B10.2 and B11.1 (5'-HEX)/B11.4, as described by Moon et al., (1999). The apparent size of microsatellite PCR fluorescent-labelled products was measured relatively to within an estimated 0.3 nucleotide units by capillary electrophoresis using an ABI 3100 Genetic Analyzer with POP6 polymer chemistry in 50 cm capillary arrays and GeneScan-400HD standards (Applied Biosystems Inc., Foster City, Calif.).

The apparent sizes of PCR products by this technique (adjusted by subtracting a unit where an adenine nucleotide appears to have been terminally added) are in Table 4 and show that the endophytes of this invention may be distinguished from other groups of *N. lolii* endophytes by the apparent sizes of alleles. Thus the strains of this invention may be characterised by B10 allele of apparent size about 160.6 and a B11 allele of apparent size about 132.0. Other strains of *N. lolii* and some of *Epichloë festucae* have been shown to generally have a single B10 allele with apparent size about 175.6 and a single variable apparent sized B11 allele although the size 132.0 was not observed in any endophyte outside the endophytes of this invention. A single allele for each locus is typical of *N. lolii* and *Epichloë festucae*.

TABLE 4

Apparent size of B10 and B11 microsatellite PCR products

| Source material | B10 allele size | B11 allele size |
|---|---|---|
| *N. lolii* strain Lp19 | 175.7 | 180.3 |
| *N. lolii* strain Lp7 | 175.6 | 188.3 |
| AR29 (*N. lolii* strain from Grasslands Nui ryegrass) | 175.7 | 176.2 |
| AR5 (a strain lacking lolitrem B) | 175.6 | 240.7 |
| AR1 (a strain lacking both lolitrem B and ergovaline) | 175.7 | 147.8 |
| Fl1 (*Epichloëfestucae* from *Festuca longifolia*) | 175.6 | 115.6 |
| AR37 | 160.6 | 132.0 |
| AR40 | 160.7 | 132.0 |

The finding of single sizes of alleles (B10=c. 160.6 and B11=c. 132.0) for endophytes of this invention does not preclude a possibility that closely related endophytes with the same functional properties might have different alleles.

Analysis by AFLP (Griffiths et al., 1999) also confirmed that endophyte examples AR37 and AR40 of this invention are from a sub-group that can be distinguished from other *N. lolii* endophytes outside this sub-group by one or more polymorphic differences from within more than 200 AFLP bands observed to be polymorphic for the genus *Neotyphodium*.

Endophyte and Growth of Pasture

The growth of the cultivar Grasslands Nui infected with AR37 and wild-type, and endophyte-free was assessed in a series of field trials, both grazed and mown, in four regions of New Zealand over a period of more than 3 years from 1996.

Plots infected with AR37 generally yielded more ryegrass herbage than wild-type plots. In 11 trials sown in 1996 and 1997 annual yields measured from AR37 plots were on average 11% greater over 3 years. The greatest differences occurred from late summer through autumn.

For example, in Site 1, where conditions are favourable for good ryegrass growth (e.g. wild-type yields 15000 kg DM/ha/ year), AR37 plots yielded 6% more annual herbage (P<0.05) with the greatest yield advantages in the autumn (Table 5). At another site, Site 2, less favourable for ryegrass growth and persistence (e.g. wild-type yields 8700 kg DM/ha/year), AR37 plots had higher yields in all seasons and significantly so for 3 seasons and for total annual yields (Table 5).

TABLE 5

Ryegrass yields of Grasslands Nui infected with AR37 relative to yields of Nui with wild-type endophyte (=100) for field plots at two contrasting locations. Average of yields for 3 years for trials sown in autumn 1996

| Site | Winter | Spring | Summer | Autumn | Annual |
|------|--------|--------|--------|--------|--------|
| Site 1 | 108 | 100 | 107 | 120* | 106* |
| Site 2 | 113 | 114* | 117* | 123* | 116* |

*Indicates value at the site is significantly different to wild-type (P < 0.05)

At Site 2, another trial sown in 1998 with Nui ryegrass and a ryegrass selection known as 'GA66' resulted in higher annual yields for AR37 plots for both ryegrasses (+15% and +14%) (P<0.05) compared with wild-type plots.

Differences in number of tillers were apparent from midsummer to early winter, being from 22% to 64% greater for AR37 compared with wild-type (P<0.05) (Table 6).

TABLE 6

Grasslands Nui ryegrass tiller numbers in autumn (per meter row at Site 3, per m$^2$ at site 1)

| Site | AR37 | Wild-type | Endophyte-free |
|------|------|-----------|----------------|
| Site 3, Area 1 | 1340$^a$ | 1100$^b$ | 1120$^b$ |
| Site 3, Area 2 | 1680$^a$ | 1300$^b$ | 1030$^b$ |
| Site 1 | 7200$^a$ | 4400$^b$ | 4100$^b$ |

For each site numbers without a letter in common are significantly different ( P < 0.05)

For each site numbers without a letter in common are significantly different (P<0.05)

Total root organic matter was examined in a trial at Site 3 after Grasslands Nui rows were occasionally mown to simulate rotational grazing. Cores, 25 mm diameter by 300 mm soil depth were assessed and the grass infected with AR37 shown to have significantly more root mass than either endophyte-free or wild-type infected grass (Table 7).

TABLE 7

Root mass (grams organic dry matter per core)

| | AR37 | Wild-type | Endophyte-free |
|---|------|-----------|----------------|
| Total root organic matter | 2.05$^a$ | 1.39$^b$ | 1.42$^b$ |

Numbers without a letter in common are significantly different ( P < 0.05)

Numbers without a letter in common are significantly different (P<0.05)

Thus it was shown that infection of perennial ryegrass cultivars with AR37 results in generally superior pasture growth and potential pasture productivity especially in late summer and autumn.

Endophyte and Growth of Turf

Perennial ryegrass is frequently used as a main component of utility turf for aesthetic and recreational purposes. An observation that Grasslands Nui cultivar infected with AR37 had persistence and green colour compared to other endophyte infections of Grasslands Nui during a dry summer season in a further site, Site 4, stimulated a small plot trial comparison of Grasslands Nui infected with either its own natural high level of wild-type endophyte or artificially infected with AR37. Trials were conducted at Site 4 and at Site 1.

The plots were managed to simulate turf growth conditions and typical turf management with regular mowing to 2 cm height when the height had grown to an estimated 3 cm. Fertiliser was applied at 30 units of nitrogen per month generally when raining and discontinued during drought periods. Water was applied only to avoid plant death from desiccation.

The measurements made included tiller density, grass production (mowing), observations on disease and pests, soil moisture and bulk density, root mass and top mass (under the mower height) and plant morphology measurements including leaf and sheath dimensions.

Although there was little difference in yield above mower height there were differences in grass mass below mower height, particularly at Site 1 where the AR37 plot was about double the wild-type treatment (P<0.001).

The tiller density per unit of area at both Site 1 and Site 4 was significantly greater for AR37 plots (P<0.005). Similarly root mass was consistently higher with AR37 plots by about 25% or more (P<0.02) at both sites. Leaf (P<0.03) and sheath (P<0.02) widths, measured at the base of each part, were consistently less for AR37 plots measured just at Site 4. The mean tiller dry matter for AR37 was approximately 40% less than for wild-type (P<0.014) at Site 4 however the mean number of leaves per tiller was very nearly three for both endophyte plots and not significantly different.

Thus it was shown that infection with AR37 of Grasslands Nui results in a denser sward of smaller tillers when managed as a turf. These swards have increased root mass and herbage below cutting height compared to wild-type endophyte. These characteristics have high utility for improving the ground cover and lateral shear strength of turf systems.

Endophyte and Pest Protection

The endophytes of this invention provide their host perennial ryegrass with resistance to a range of insect pests including Argentine stem weevil, black beetle, mealy bug and root aphid. In a combination of field and pot trials the degree of protection provided by the AR37 endophyte when compared with endophyte-free ryegrass is equivalent to that provided by the naturally occurring wild-type endophyte for all these pests except root aphid against which the wild-type endophyte provides little or no protection (Table 8).

For Argentine stem weevil (Listronotus bonariensis) the mode of resistance afforded by endophyte differs between AR37 and the wild-type. In AR37 adult feeding and oviposition are the same as in endophyte-free plants whereas in the wild-type defence against the weevil is mediated primarily via deterrence of the adult from feeding and oviposition by the alkaloid peramine. Observations indicate that AR37 reduces larval damage to tillers because it is toxic to larvae. AR37 has been tested against Argentine stem weevil extensively in field and in pot trials and has consistently reduced damage by this pest to low levels when compared to damage in endophyte-free ryegrass.

AR37 also reduces black beetle (Heteronychus arator) damage by larvae in the field, mainly through deterrence of the adult. Adult black beetle damage to ryegrass tillers infected with AR37 was 17.3% whereas 46% of endophyte-free tillers were damaged. Survival of root aphid (Aploneura lentisci), mealy bug (Balanococcus poae) and porina (Wiseana cervinata) are also less on ryegrass with AR37 than on endophyte-free ryegrass.

TABLE 8

Examples of the effect of AR37 on different insect pests

| Insect | Parameter | AR37 | Wild-type | Endophyte-free |
| --- | --- | --- | --- | --- |
| Argentine stem weevil | % Tillers with larval damage | 13$^a$ | 17$^a$ | 36$^b$ |
| Black beetle | No. larvae/m$^2$ | 13.8$^a$ | 13.8$^a$ | 60.0$^b$ |
| Root aphid | Log (n + 1)/plant | 0.27$^a$ | 1.61$^b$ | 2.13$^b$ |
| Mealy bug | No./10 cores | 0.3$^a$ | 0.6$^b$ | 16.8$^b$ |
| Porina | % survival | 50.2$^a$ | 60.0$^{ab}$ | 89.5$^b$ |

For each insect, numbers without a letter in common are significantly different ( P < 0.05)

For each insect, numbers without a letter in common are significantly different (P<0.05)

Endophyte and Animal Performance

Sheep grazing ryegrass cultivars with their wild-type endophyte in summer and autumn may exhibit one or all of the symptoms of ryegrass-endophyte toxicosis. These include reduced live weight gain, ryegrass staggers, increased rectal temperatures and respiration rates, especially in warm humid conditions, increased incidence of faecal soiling (dags) and fly strike and reduced basal prolactin levels. Using these parameters, the health and production responses of sheep grazing the same ryegrass cultivar without endophyte, with its wild-type endophyte or with AR37 endophyte in summer and autumn over 3 years were compared (Table 9).

TABLE 9

Mean responses (3 years) of sheep grazing ryegrass with AR37 compared to same ryegrass without endophyte or with its wild-type endophyte

|  | Endophyte-free | Wild-type | AR37 |
| --- | --- | --- | --- |
| Live weight change (g/day) | 62 | −12 | 47 |
| Ryegrass staggers (0-5 ascending scale) | 0 | 2.7 | 1.8 |
| Rectal temperature (° C.) | 40.4 | 40.7 | 40.5 |
| Respiration rate (breaths/minute) | 85 | 109 | 95 |
| Plasma prolactin (ng/ml) | 208 | 110 | 210 |

The sheep grazing endophyte-free ryegrass exhibited none of the adverse responses typically associated with ryegrass-endophyte toxicosis. Those grazing ryegrass with AR37 had mild ryegrass staggers but the incidence and severity was significantly less than for those sheep grazing ryegrass with its wild-type endophyte. Mean live weight change was slightly lower than for those grazing endophyte-free but significantly better than the negative growth rates of those grazing ryegrass with wild-type endophyte. For all the other parameters (rectal temperature, respiration rate and plasma prolactin levels) measured there was no significant difference between sheep grazing endophyte-free ryegrass and those grazing ryegrass with AR37. However respiration rates and rectal temperatures were significantly higher for sheep grazing ryegrass with its wild-type endophyte than for those grazing AR37, while plasma prolactin levels were significantly lower for ryegrass with wild-type endophytes.

In another replicated trial there was no evidence of ryegrass staggers in sheep grazing endophyte-free ryegrass cultivars with AR37 whereas on the same ryegrass cultivars with wild-type endophyte the sheep had serious ryegrass staggers. Mean live weight gains in sheep grazing AR37 treatments were 130 g/day whereas those grazing the same ryegrass with its wild-type endophyte grew at only 90 g/day.

In a larger on-farm grazing trial where the ryegrass was sown with clover, responses were similar in sheep grazing AR37 treatments to those on endophyte-free treatments with no ryegrass staggers on AR37 treatments.

Aspects of the present invention have been described by way of example only and it should be appreciated that modifications and additions may be made thereto without departing from the scope thereof as defined in the appended claims.

REFERENCES

Ball, O. J-P.; Miles, C. O.; Prestidge, R. A. 1997: Ergopeptine alkaloids and Neotyphodium lolii-mediated resistance in perennial ryegrass against Heteronychus arator (Coleoptera: Scarabaeidae). Journal of Economic Entomology 90: 1383-1391.

Barker, D. J.; Davies, E.; Lane, G. A.; Latch, G. C. M.; Nott, H. M.; Tapper, B. A. 1993: Effect of water deficit on alkaloid concentrations in perennial ryegrass endophyte associations. In Proceedings of the Second International Symposium on Acremonium/Grass Interactions. Eds. Hume, D. E.; Latch, G. C. M.; Easton, H. S. AgResearch, New Zealand, pp. 67-71.

Belofsky, G. N.; Gloer, J. B.; Wicklow, D. T.; Dowd, P. D. 1995: Antiinsectan alkaloids: shearinines A-C and a new paxilline derivative from the ascostromata of Eupenicillium shearii. Tetrahedron, 51: 14, 3959-3968.

Blank, C. A.; Gwinn, K. D. 1992: Soilborne seedlings diseases of tall fescue: influence of the endophyte Acremonium coenophialum. Phytopathology 82: 1089.

Bouton, J. H.; Latch, G. C. M.; Hill, N. S.; Hoveland, C. S.; McCann, M. A.; Watson, R. H.; Parish, J. H.; Hawkins, L. L.; Thompson, F. N. 2002: Re-infection of tall fescue cultivars with non-ergot alkaloid-producing endophytes. Agronomy Journal 94: 567-574.

de Jesus, A. E.; Steyn, P. S.; van Heerden, F. R.; Vleggaar, R. 1984: Structure elucidation of the janthitrems, novel tremorgenic mycotoxins from Penicillium janthinellum. Journal of the Chemical Society, Perkin Transactions I., 4, 697-701.

Elberson, H. W.; West, C. P. 1996: Growth and water relations of field grown tall fescue as influenced by drought and endophyte. Grass and Forage Science 51: 333-342.

Fletcher, L. R. 1999: "Non-toxic" endophytes in ryegrass and their effect on livestock health and production. In Ryegrass endophyte: an essential New Zealand symbiosis. Grassland Research and Practice Series No. 7, pp 133-139.

Fletcher, L. R.; Easton, H. S. 2000: Using Endophytes for Pasture Improvement in New Zealand. In Proceedings of The Grassland Conference 2000, 4th International Neotyphodium/Grass Interactions Symposium. Eds. Paul, V. H.; Dapprich, P. D. Universtät, Paderborn, pp 149-162.

Fletcher, L. R.; Sutherland, B. L.; Fletcher, C. G. 1999: The impact of endophyte on the health and productivity of sheep grazing ryegrass-based pastures. In Ryegrass endophyte: an essential New Zealand symbiosis. Grassland Research and Practice Series No. 7, pp 11-17.

Gallagher, R. T.; Latch, G. C. M.; Keogh, R. G. 1980: The janthitrems: fluorescent tremorgenic toxins produced by Penicillium janthinellum isolates from ryegrass pastures. Applied and Environmental Microbiology, 39: 1, 272-273.

Griffiths, A.; Moon, C.; Tapper, B.; Christensen, M. 1999: Non-radioactive AFLP fingerprinting for detection of genetic variation in Epichloë/Neotyphodium endophytes. Proceedings of the 11th Australian Plant Breeding Conference.

Latch, G. C. M.; Christensen, M. J. 1985: Artificial infection of grasses with endophytes. Annals of Applied Biology 107: 17-24.

Leuchtmann, A. 1997: Ecological diversity in *Neotyphodium*-infected grasses as influenced by host and fungus characteristics. In *Neotyphodium*/Grass Interactions, Eds. Bacon, C. W.; Hill, N. S. Plenum Press, New York, pp 93-108.

Moon, C. D.; Tapper, B. A.; Scott, D. B. 1999: Identification of Epichloë endophytes in planta by a microsatellite-based PCR fingerprinting assay with automated analysis. Applied and Environmental Microbiology 65: 1268-1279.

Penn, J., Swift, R.; Wigley, L. J.; Mantle, P. G.; Bilton, J. N.; Sheppard, R. N. 1993: Janthitrems B and C, two principal indole-diterpenoids produced by Penicillium janthinellum. Phytochemistry, 32: 6, 1431-1434.

Prestidge, R. A.; Gallagher, R. T. 1985: Lolitrem B—a stem weevil toxin isolated from *Acremonium*-infected ryegrass. Proceedings 38th New Zealand weed and pest control conference: 38-40.

Rowan, D. D.; Dymock, J. J.; Brimble, M. A. 1990: Effect of fungal metabolite peramine and analogs on feeding and development of Argentine stem weevil (Listronotus bonariensis). Journal of Chemical Ecology 16: 1683-1695.

Rowan, D. D.; Hunt, M. B.; Gaynor, D. L. 1986: Peramine, a novel insect feeding deterrent from ryegrass infected with the endophyte *Acremonium loliae*. Journal of the Chemical Society. Chem. Commun. 1986. 935-936.

Rowan, D. D.; Latch, G. C. M. 1994: Utilization of endophyte-infected perennial ryegrasses for increased insect resistance. In Biotechnology of endophyte fungi in grasses. Eds. Bacon, C. W. White, J. CRC Press, pp 169-183.

Siegel, M. R.; Latch, G. C. M.; Bush, L. P.; Fannin, F. F.; Rowan, D. D.; Tapper, B. A.; Bacon, C. W.; Johnson, M. C. 1990: Fungal endophyte-infected grasses: alkaloid accumulation and aphid response. Journal of Chemical Ecology 16: 3301-3315.

Spiering, M. J.; Davies, E.; Tapper, B. A.; Schmid, J.; Lane, G. A. 2002: Simplified extraction of ergovaline and peramine for analysis of tissue distribution in endophyte-infected grass tillers. Journal of Agricultural and Food Chemistry, 50: 5856-5862.

Stuedemann, J. A.; Hoveland. C. 1988: Fescue endophyte: History and impact on animal agriculture. Journal of Production Agriculture 1: 39-44.

Tapper, B. A.; Latch, G. C. M. 1999: Selection against toxin production in endophyte-infected perennial ryegrass. In Ryegrass endophyte: an essential New Zealand symbiosis. Grassland Research and Practice Series No. 7, pp 107-111.

Wilkins, A. L.; Miles, C. O.; Ede R. M.; Gallagher, R. T.; Munday, S. C. 1992: Structure elucidation of janthitrem B, a tremorgenic metabolite of Penicillium janthinellum, and relative configuration of the A and B rings of janthitrems B, E, and F. Journal of Agricultural and Food Chemistry, 40: 8, 1307-1309.

What is claimed is:

1. A method of protecting a host grass from stress, comprising artificially inoculating the host grass with one or more biologically pure *Neotyphodium lolii* endophyte strains wherein the *Neotyphodium lolii* endophyte strain produces at least one epoxy janthitrem G compound at a level sufficient to confer protection to the host grass.

2. The method of claim 1 wherein said epoxy janthitrem G compound is 11,12-epoxy-janthitrem G.

3. The method of claim 1, wherein the artificially inoculated host grass has enhanced root growth and more tillers in comparison to a grass without endophyte inoculation.

4. The method of claim 1, wherein the stress is a biotic stress caused by at least one organism selected from the group consisting of a pest and an insect.

5. The method of claim 4, wherein the pest is selected from the group consisting of: Aploneura lentisci; Balanococcus poae; Heteronychus arator; Wiseana cervinata; and combinations thereof.

6. The method of claim 1, wherein the endophyte strain confers to the host grass at least one feature selected from the group consisting of enhancement of grazing, animal growth and increased animal productivity, in comparison with grass infected with endophytes that induce ryegrass-endophyte toxicosis.

7. The method of claim 1, wherein the stress is abiotic stress caused by water deficit.

8. The method of claim 1, wherein the host grass is a perennial, annual or hybrid ryegrass.

9. The method of claim 1, wherein the host grass is a Pooideae grass.

10. The method of claim 9, wherein the host Pooideae grass is selected from the group consisting of the species: *Lolium perenne; Lolium multifloum*; and *Lolium×hybridum*.

11. The method of claim 1, wherein the endophyte strain does not produce sufficient levels of a compound or compounds to cause toxicosis in grazing animals.

12. The method of claim 11 wherein the toxicosis is ryegrass-endophyte toxicosis.

13. The method of claim 12, wherein the toxicosis avoided is caused by a toxin selected from the group consisting of ergovaline toxin, lolitrem toxin, and a combination thereof.

14. The method of claim 1, wherein the endophyte strain produces toxic alkaloids lolitrem B and ergovaline at detection levels of less than 2 ppm of dry matter lolitrem B and 0.5 ppm of dry matter ergovaline.

15. The method of claim 1, wherein the endophyte strain produces toxic alkaloids lolitrem B and ergovaline at detection levels of less than 0.1 ppm of dry matter of said lolitrem B and ergovaline.

16. The method of claim 1, wherein the *Neotyphodium lolii* endophyte strains have base pair allele sizes of 160-161 at the B10 allele and 131.5 to 132.5 at the B11 allele.

* * * * *